US010085743B2

(12) United States Patent
Roedl et al.

(10) Patent No.: US 10,085,743 B2
(45) Date of Patent: Oct. 2, 2018

(54) STAPLE IMPLANT FOR INFLUENCING THE GROWTH IN BONE REGIONS BORDERING AN EPIPHYSEAL PLATE

(71) Applicants: MERETE MEDICAL GMBH, Berlin (DE); UNIVERSITÄTSKLINIKUM MÜNSTER, Münster (DE)

(72) Inventors: Robert Roedl, Munster (DE); Emmanuel Anapliotis, Berlin (DE); Susanne Kahl, Berlin (DE)

(73) Assignee: Aristotech Industries GmbH, Luckenwalde (DE)

( * ) Notice: Subject to any disclaimer, the term of this patent is extended or adjusted under 35 U.S.C. 154(b) by 297 days.

(21) Appl. No.: 14/772,709

(22) PCT Filed: Apr. 2, 2014

(86) PCT No.: PCT/DE2014/100115
§ 371 (c)(1),
(2) Date: Sep. 3, 2015

(87) PCT Pub. No.: WO2014/161533
PCT Pub. Date: Oct. 9, 2014

(65) Prior Publication Data
US 2016/0015384 A1    Jan. 21, 2016

(30) Foreign Application Priority Data

Apr. 4, 2013 (DE) .................. 10 2013 005 632
Sep. 27, 2013 (DE) .................. 10 2013 110 759

(51) Int. Cl.
*A61B 17/064* (2006.01)
*A61B 17/00* (2006.01)

(52) U.S. Cl.
CPC *A61B 17/0642* (2013.01); *A61B 2017/00477* (2013.01); *A61B 2017/00946* (2013.01)

(58) Field of Classification Search
CPC .................. A61B 17/064–2017/0646
See application file for complete search history.

(56) References Cited

U.S. PATENT DOCUMENTS

| 2,111,404 A | * | 3/1938 | Pankonin | B65D 9/32 206/340 |
| 3,519,419 A | * | 7/1970 | Gibson | C21D 8/005 148/428 |

(Continued)

FOREIGN PATENT DOCUMENTS

| DE | 3310833 A1 | 10/1983 |
| EP | 0033641 A2 | 8/1981 |

(Continued)

OTHER PUBLICATIONS

International Preliminary Report on Patentability with English translation, PCT/DE2014/100115, dated Oct. 6, 2015.

(Continued)

*Primary Examiner* — Zade Coley
(74) *Attorney, Agent, or Firm* — Andrus Intellectual Property Law, LLP (57) ABSTRACT

A staple implant is for influencing or guiding the growth in bone regions bordering the epiphyseal plate, said staple having a transverse web and anchoring limbs arranged on the ends of the transverse web, running parallel to one another and terminating in points. The anchoring limbs, once inserted into the bone, form fixation points on one side of said bone on either side of the epiphyseal, plate. The transverse web has at least one narrowed zone that can be plastically deformed under a flexural load, said zone having any position and form without abrupt transitions and being situated between the fixation points.

5 Claims, 9 Drawing Sheets

(56) References Cited

U.S. PATENT DOCUMENTS

| | | | | |
|---|---|---|---|---|
| 4,187,609 | A | * | 2/1980 | Edelman ............... A61C 8/001 433/176 |
| 4,263,903 | A | * | 4/1981 | Griggs ............... A61B 17/0642 227/147 |
| 4,438,769 | A | * | 3/1984 | Pratt ............... A61B 17/0642 227/147 |
| 4,444,181 | A | * | 4/1984 | Wevers ............... A61B 17/0642 606/75 |
| 4,454,875 | A | * | 6/1984 | Pratt ............... A61B 17/0642 606/219 |
| 4,848,328 | A | * | 7/1989 | Laboureau ......... A61B 17/0642 606/75 |
| 4,878,915 | A | * | 11/1989 | Brantigan .......... A61B 17/1604 606/247 |
| 4,994,063 | A | * | 2/1991 | Garner ............... A61B 17/0642 606/75 |
| 5,246,443 | A | | 9/1993 | Mai |
| 5,449,359 | A | | 9/1995 | Groiso |
| 5,454,814 | A | * | 10/1995 | Comte ............... A61B 17/0642 606/219 |
| 5,993,476 | A | | 11/1999 | Groiso |
| 6,116,070 | A | * | 9/2000 | Oshida ............... A61C 8/0048 433/200.1 |
| 6,179,840 | B1 | * | 1/2001 | Bowman ............ A61B 17/0401 128/899 |
| 6,277,149 | B1 | * | 8/2001 | Boyle ............... A61F 2/4465 623/16.11 |
| 8,029,507 | B2 | | 10/2011 | Green et al. |
| 8,133,230 | B2 | | 3/2012 | Stevens et al. |
| 2003/0139746 | A1 | * | 7/2003 | Groiso ............... A61B 17/0642 606/75 |
| 2004/0138705 | A1 | * | 7/2004 | Heino ............... A61B 17/064 606/219 |
| 2005/0273108 | A1 | * | 12/2005 | Groiso ............... A61B 17/0642 606/75 |
| 2008/0232929 | A1 | * | 9/2008 | Jackson ............... F16B 15/0015 411/476 |
| 2010/0237128 | A1 | * | 9/2010 | Miller ............... A61B 17/0642 227/175.1 |
| 2011/0029016 | A1 | * | 2/2011 | Yeung ............... A61B 17/0401 606/219 |
| 2011/0160766 | A1 | * | 6/2011 | Hendren ............ A61B 17/0487 606/232 |

FOREIGN PATENT DOCUMENTS

| | | |
|---|---|---|
| EP | 0127994 A1 | 12/1984 |
| EP | 0586313 A1 | 3/1994 |
| EP | 0852128 A1 | 7/1998 |
| EP | 0955011 A1 | 11/1999 |
| FR | 2562416 A1 | 10/1985 |
| FR | 2628312 A1 | 9/1989 |
| FR | 2934147 A1 | 1/2010 |
| FR | 2982142 A1 | 5/2013 |
| WO | 2004107991 A1 | 12/2004 |
| WO | 2012040863 A1 | 4/2012 |

OTHER PUBLICATIONS

International Search Report for PCT/DE2014/100115 dated Aug. 7, 2014.

* cited by examiner

STAPLE IMPLANT FOR INFLUENCING THE GROWTH IN BONE REGIONS BORDERING AN EPIPHYSEAL PLATE

CROSS-REFERENCE TO RELATED APPLICATIONS

This application is the U.S. national stage application of International Application PCT/DE2014/100115, filed Apr. 2, 2014, which international application was published on Oct. 9, 2014, as International Publication WO2014/161533. The international application is incorporated herein by reference, in entirety. The international application claims priority to German Patent Application No. 102013005632.2, filed Apr. 4, 2013, and German Patent Application No. 102013110759.1, filed. Sep. 27, 2013, which are incorporated herein by reference, in entirety.

The invention relates to a staple implant for influencing the growth in bone regions bordering an epiphyseal plate.

BACKGROUND

The prior art discloses a whole series of implants with which it is attempted to correct axial misalignment in children and adolescents before completion of the growth phase (for example U.S. Pat. Nos. 8,133,230 B2, 8,029,507 B2). These have the disadvantage of being composed of a large number of parts and of entailing high production costs. Moreover, the bulky connection parts, designed like joints, and the corresponding screws cause increased trauma to the patient during the implantation.

Moreover, rigid bone staples are known for guiding the bone growth at the epiphyseal plate (Blount staples), these having two parallel anchoring limbs connected to each other by a common rectilinear transverse web (EP 0 033 641 B1, EP 0 127 994 B1, EP 0 586 313 B1, EP 0 852 128 B1, DE 33 10 833 C2, U.S. Pat. Nos. 5,246,443 A, 5,449,359 A, WO 2004/107991 A1). These staples are primarily used in temporary epiphyseodesis, in which at least two staples are applied transversely, and parallel to each other, to the epiphyseal plate under X-ray monitoring, the aim being to block the growth thereof locally in the area of the staple.

Although these known staples permit inhibition of growth by exerting compression on the bone regions lying opposite each other, they do not allow simultaneous bending open of the transverse web of the staples in order to deliberately promote the growth at the epiphyseal plate lying opposite the staple region.

SUMMARY

An object of the invention is to make available a staple implant which permits a deformational bending of the transverse web, in order to deliberately open the epiphyseal plate lying opposite the staple area and to provide improved guidance of the growth, and which at the same time permits a reduction in the number of parts, is easier for the surgeon to handle and entails reduced costs.

A staple implant is provided for influencing the growth in bone regions bordering an epiphyseal plate. The staple implant has a transverse web, and anchoring limbs which are arranged at the ends of the transverse web, are oriented parallel to each other and terminate in points. The anchoring limbs, after they have been inserted into the bone, form fixation points on one side of said bone, to both sides of the epiphyseal plate. The transverse web has at least one tapered or narrowed zone, which is plastically deformable under a flexural load and which is configured in any desired position and shape without abrupt transitions between the fixation points.

This ensures that the staple bends open between its fixation points, as a result of the growth forces acting on the epiphyseal plate lying opposite the staple area, and does not impede the growth by compression.

A main axis of bending here preferably runs transversely with respect to the connection line between the anchoring limbs.

The staple implant can be made of a superplastic biocompatible material, preferably titanium, a titanium alloy with nanocrystalline to ultrafine-grained grain size (1 nm to 1 µm). These materials achieve a high degree of strength in combination with sufficiently high ductility and a low tendency to fatigue.

The tapered or narrowed zone can be formed symmetrically or asymmetrically with respect to the longitudinal axis in the transverse web. In this way, the bending properties of the tapered zone can be influenced by its form and shape on the top face and lower face of the transverse web, such that growth can be guided in a targeted manner according to the size and extent of the axial misalignment presented by the patient.

Blind bores with internal threading can be introduced, in alignment with the limb axes, into the transverse web in order to allow an impaction instrument to be connected to the transverse web with a force fit and in order to accordingly apply the staple implant no the epiphyseal plate.

Alternatively, the transverse web can be provided with a circumferential bead or groove for securing it by clamping on an impaction instrument, and the blind holes can be provided with internal threading for securing an extraction instrument.

After it has bent open, and as a result of the growth forces, the bending area of the narrowed zone has a cross section that can be easily separated with a separating instrument prior to the extraction of the implant.

The transverse web and the anchoring limbs can have the same or different cross-sectional shapes, for example round, square or polygonal profiles.

The anchoring limbs can each be formed with a through-channel extending in the longitudinal direction of the anchoring limbs. The through-channel extends preferably axially symmetrically in the respective anchoring limb. The one or more through-channels can be used for applying K-wires during the implantation.

The through-channel, in one or both anchoring limbs, can have an internal thread at least in part. In this way, it is possible to screw a working tool into the anchoring limb, for example during deliberate removal of the staple implant.

The anchoring limbs, at least on parts of their outer surface, can have anchoring means with protruding surface contours. The anchoring means, which counteract inadvertent loosening of the anchoring limbs after the staple implant has been secured on the bone, can extend along the entire length of the respective anchoring limb.

The transverse web can be formed, at least in a central area in which the narrowed zone is optionally arranged, with a flat profile in cross section. In this or other embodiments, the transverse web can have a web thickness of approximately 0.5 to approximately 3 mm, preferably of approximately 0.5 to approximately 1 mm, in the area of the narrowed zone.

In one embodiment, the transverse web can be formed, at least in the central area, with a flat profile in cross section. In this embodiment, the web thickness corresponds to the height of the flat profile. The ratio of the web height in the central area to the web height at the ends of the transverse web can be between approximately 3 and approximately 4, preferably between approximately 3 and approximately 3.5, particularly in conjunction with use in a staple implant on one side for correction of genu valgum or genu varum. A ratio of approximately 3.3 is particularly preferable. Particularly in use on both sides (medial and lateral, for example for equalization of leg length), a ratio of approximately 0.5 to approximately 1.5, preferably of approximately 1, may be provided. In the various embodiments, the web height in the end area can be between approximately 1 and approximately 3 mm, preferably approximately 2 mm. In the central area with the flat profile, the web width can be approximately 1.5 to approximately 3 mm.

When the staple implant is viewed from above (top side), the transverse web can be wider at least in the central area compared to the ends of the transverse web.

When the staple implant is viewed from the front, the anchoring limbs can be offset parallel to each other in such a way that the anchoring limbs are arranged with the transverse web in a trapezoid shape. An angle that characterizes the derivation from a right-angled arrangement (trapezoid shape) can be between >0° and approximately 25°. An angle of approximately 18° may preferably be provided.

On their inner sides directed toward each other, the anchoring limbs can have a flat surface which is oriented transversely with respect to the connection line between the anchoring limbs, preferably at a right angle thereto. The flat surface can be free of the anchoring means.

The narrowing or tapering of the transverse web can be formed by means of a depression extending from the top side of the staple implant. In contrast to this, on the opposite and inner side, i.e. the side facing toward the bone after the implantation, the transverse web can be made flat, i.e. in particular without any depression or protrusions. In this way, a flat contact surface with the bone can be formed.

BRIEF DESCRIPTION OF ILLUSTRATIVE EMBODIMENTS

Further illustrative embodiments are explained in more detail below with reference to the figures of a drawing, in which.

DETAILED DESCRIPTION OF ILLUSTRATED EMBODIMENTS

Figure 1:
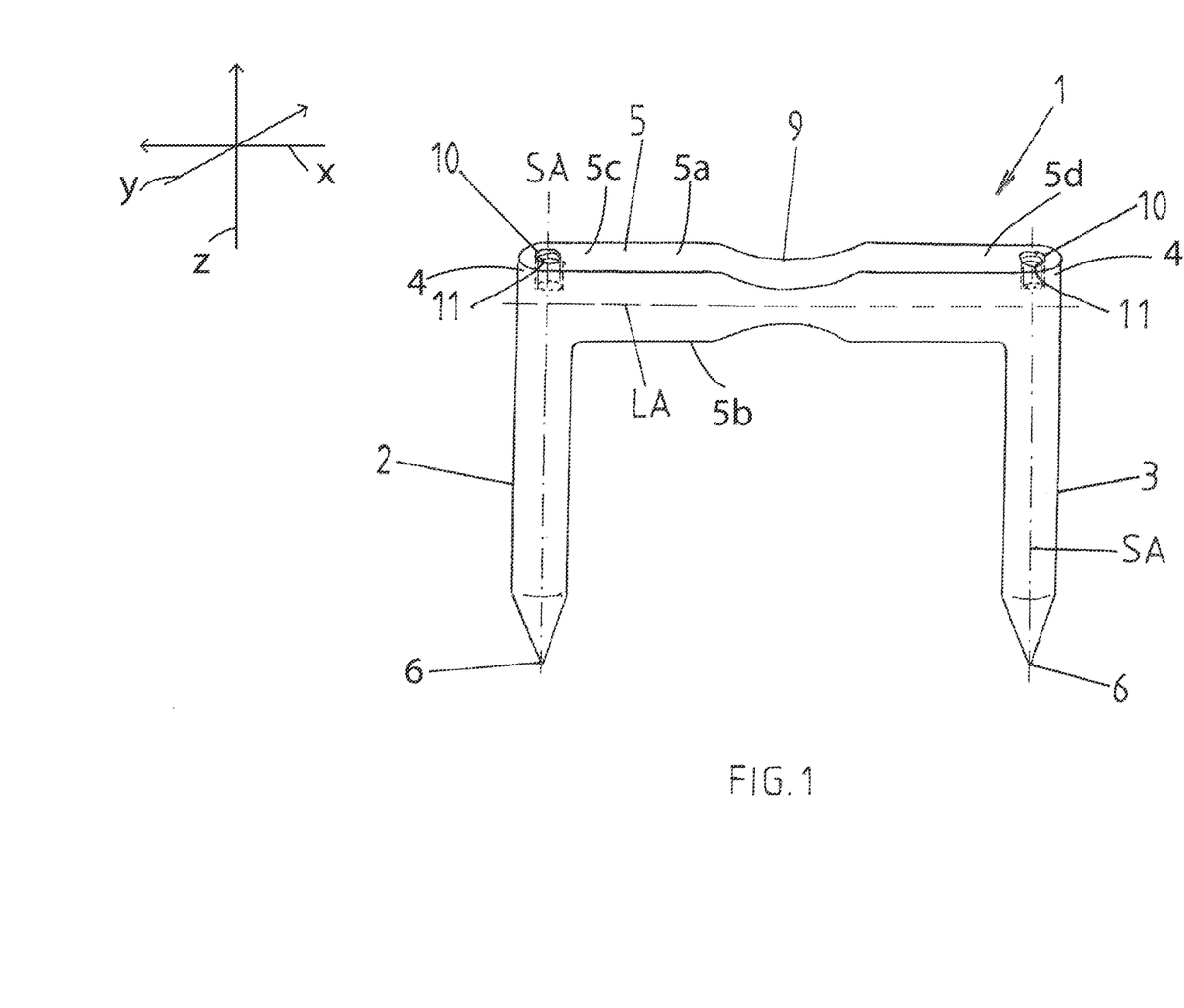
FIG. 1 shows a perspective view of a staple implant, with blind bores introduced into the face of the transverse web.

In FIG. 1, the basic structure of the one-piece staple implant 1 is shown, having the form of a solid round profile which, for example, is made of a superplastic biocompatible material. Superplastic materials are nanostructured or ultra-fine-grained materials that have grain sizes of between a few nanometers and a micrometer and that exhibit superplastic behavior, e.g. extensions of more than 100%, and even up to 1000%, along with high degrees of strength.

Pure titanium or also titanium alloys have proven particularly suitable for the present example of a staple implant. However, other biocompatible materials can also be used, for example superplastic steels.

The staple implant 1 is contoured relative to longitudinally extending x, laterally extending y, and vertically extending z axes lying perpendicular to each other, and configured for insertion into a bone at a staple area for influencing epiphyseal plate 13. The staple implant 1 has two anchoring limbs 2 and 3, which have limb axes SA oriented parallel to each other and which are connected to each other at their upper ends 4 by a transverse web 5 having a top surface 5a, a bottom surface 5b and opposed ends 5c, 5d. The lower ends 6 of the anchoring limbs 2 and 3 taper to a point and, after they have been driven into the bones to both sides of the epiphyseal plate 13, form corresponding fixation points 7 and 8.

The transverse web 5 has a tapered zone 9, provided as at least one concave formation, which extends symmetrically with respect to the longitudinal axis LA of the transverse web and forms the central part of the transverse web.

Blind holes 10 with an internal thread 11 are introduced into the transverse web 5 in alignment with the limb axis SA and each serve for securing an impaction instrument or an extraction instrument. The impaction or extraction instruments are commercially available and therefore require no further explanation.

Figure 2A:
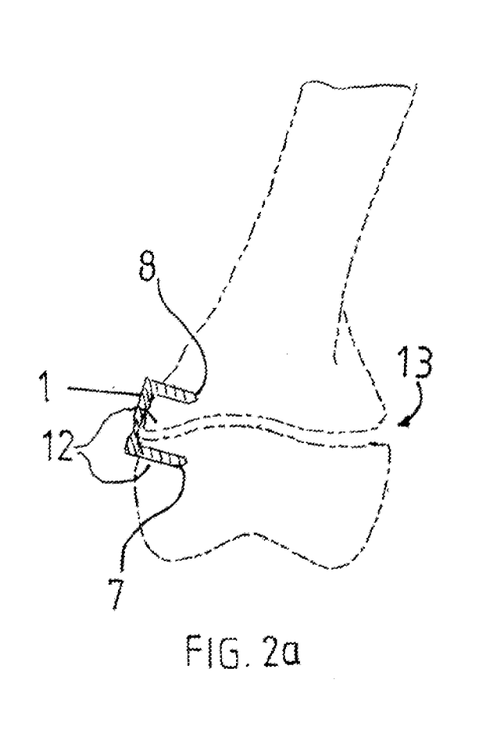
FIGS. 2a and 2b show schematic views of the bending open of the staple implant as a result of the bone growth at the epiphyseal plate lying opposite the clamped area.
Figure 2B:
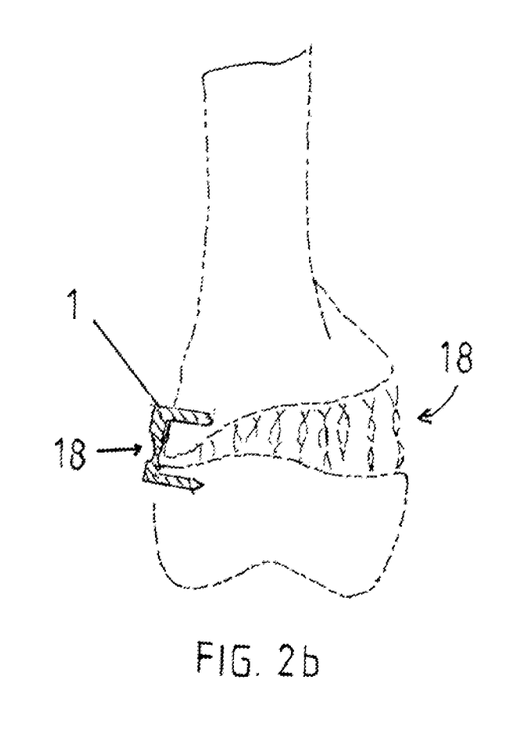

FIGS. 2a and 2b illustrate the bending open of the staple implant 1 according to the invention in the tapered zone 9, which bending open is initiated by the bone growth at the epiphyseal plate 13 lying opposite the stapled area 12. The bending area 18 of the tapered zone 9 has undergone plastic deformation, such that the anchoring limbs 2 and 3 execute an expansion movement relative to each other, which movement leads to a reduction of the load on the epiphyseal plate 13 and therefore does not impede the bone growth.

Figure 3:
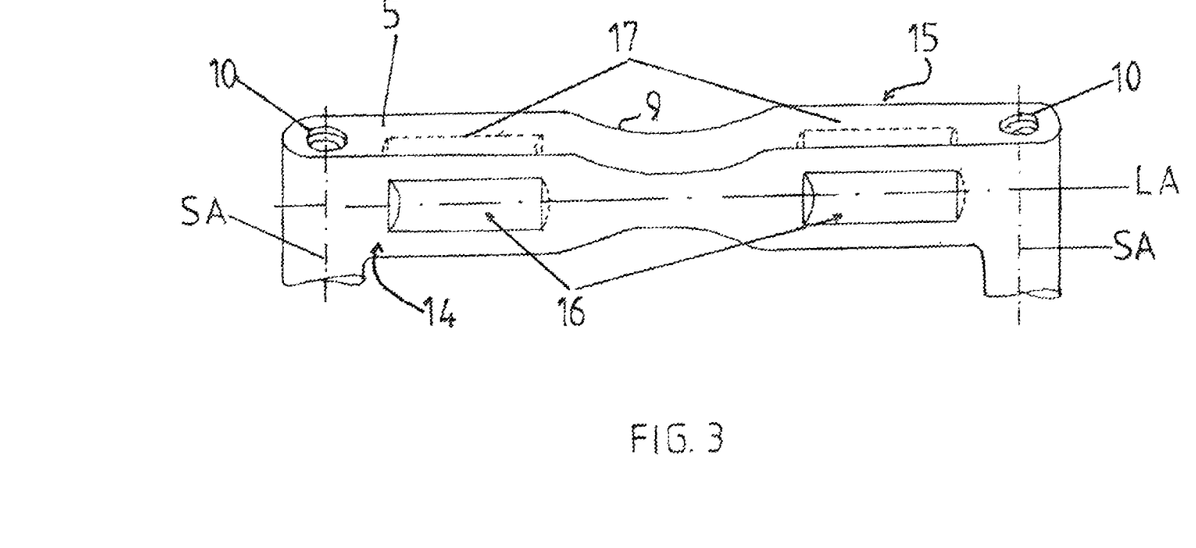
FIG. 3 shows a view of the transverse web with recesses introduced in the alignment of its longitudinal axis for securing it by clamping 20 with an impaction instrument.
Figure 4:
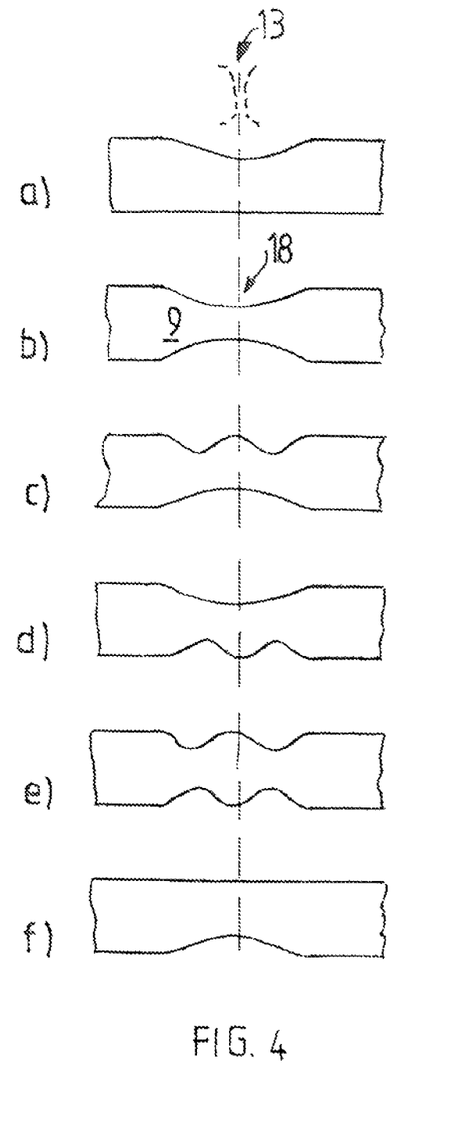
FIGS. 4a to 4f show variants or the position and shape of narrowed zones in the transverse web of the staple implant.

FIG. 3 shows by way of example a view of the transverse web 5 in which the front and rear faces of side portions 14 and 15 extending flush with the anchoring limbs 2 and 3 are each provided with two recesses 16 and 17 which are parallel to the longitudinal axis LA and in alignment with each other.

However, the invention also includes the possibility that, instead of recesses 16 and 17, corresponding beads are integrally bonded onto the front and rear faces of side portions 14 and 15 of the transverse web 5.

The recesses 16 and 17 or beads serve to transmit force when the limbs 2 and 3 are driven in with a customary impaction instrument which, with its gripping elements, engages in the recesses 16 and of the transverse web 5 to transmit force on both sides or engages around the beads and brings the staple implant 1 for impaction into position. In such a case, the blind holes 10 with their internal threads 11 are used merely to secure the extraction instrument, as a result of which the internal threads 11 are not subjected to any impact stress.

After it has bent open, the bending area 18 of the tapered zone 9 has a cross section that can be easily separated by a separating instrument, such that each anchoring limb 2, 3 can be individually removed gently by the extraction instrument.

FIGS. 4a to 4f show various shapes of the tapered zone 9 in the transverse web 5 of the staple implant 1. A symmetrical or asymmetrical arrangement of at least one tapered zone 9 can be provided, wherein sharp edges or corners should simply be avoided in the configuration of the tapered zone 9, so as to prevent a concentration of stress at the edges or corners 5. The bending area 18 of the tapered zone 9 can be assigned to that cross section which, within the tapered zone, assumes a minimum.

The staple implant 1 can be designed in various profile shapes, for example as a round, square or polygonal profile.

The staple implant, in its various configurations, has the particular advantage that the superplastic properties of the staple material, in conjunction with the particular shape and position of the tapered zone, rule out a compression effect at the epiphyseal plate 13 lying opposite the stapled area 12. Moreover, the staple implant 1 is of very simple construction and is exceptionally suitable for a minimally invasive procedure performed by the surgeon to correct a loss of axial alignment.

A further embodiment of the staple implant 1 is explained below with reference to FIGS. 5 to 9. The same reference signs as in FIGS. 1 to 4 are used for the same features in FIGS. 5 to 9.

Figure 5:
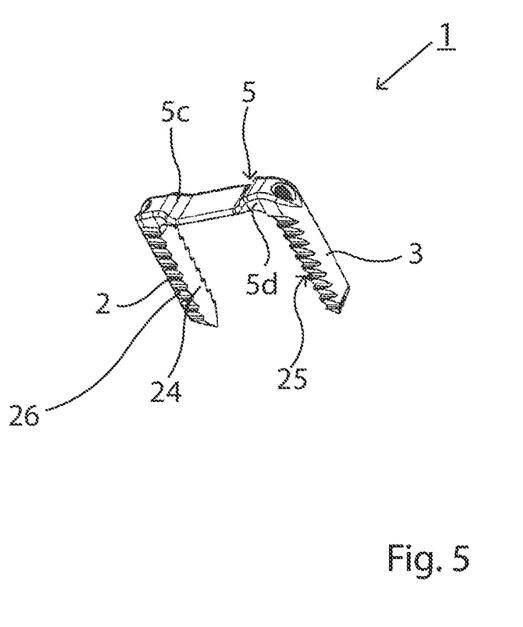
FIG. 5 shows a schematic perspective view of a further staple implant with a narrowed zone in the transverse web.

In the staple implant 1 in FIG. 5, the two anchoring limbs 2, 3 are likewise connected to each other via the transverse web 5. The transverse web 5 has the tapered zone 9 which, in the embodiment shown, is arranged centrally and symmetrically with respect to the center of the transverse web 5 by means of a depression 19, which starts from a top side 20 of the staple implant 1. In the central area 21 of the depression 19, the transverse web 5 is designed as a flat profile with a constant web height. The height of the transverse web 5 then increases again toward the ends 5c, 5d of the transverse web 5. With the tapered zone 9, a bending area is formed in such a way that the staple implant 1 is able to bend in the area of the transverse web 5 during use in connection with an epiphyseal plate, as is shown in particular in FIG. 9.

A through-channel 22, 23 extends in the axial direction through each of the anchoring limbs 2, 3, and said through-channel 22, 23 for one or both anchoring limbs 2, 3 can be provided at least in part with an internal thread.

Figure 6:
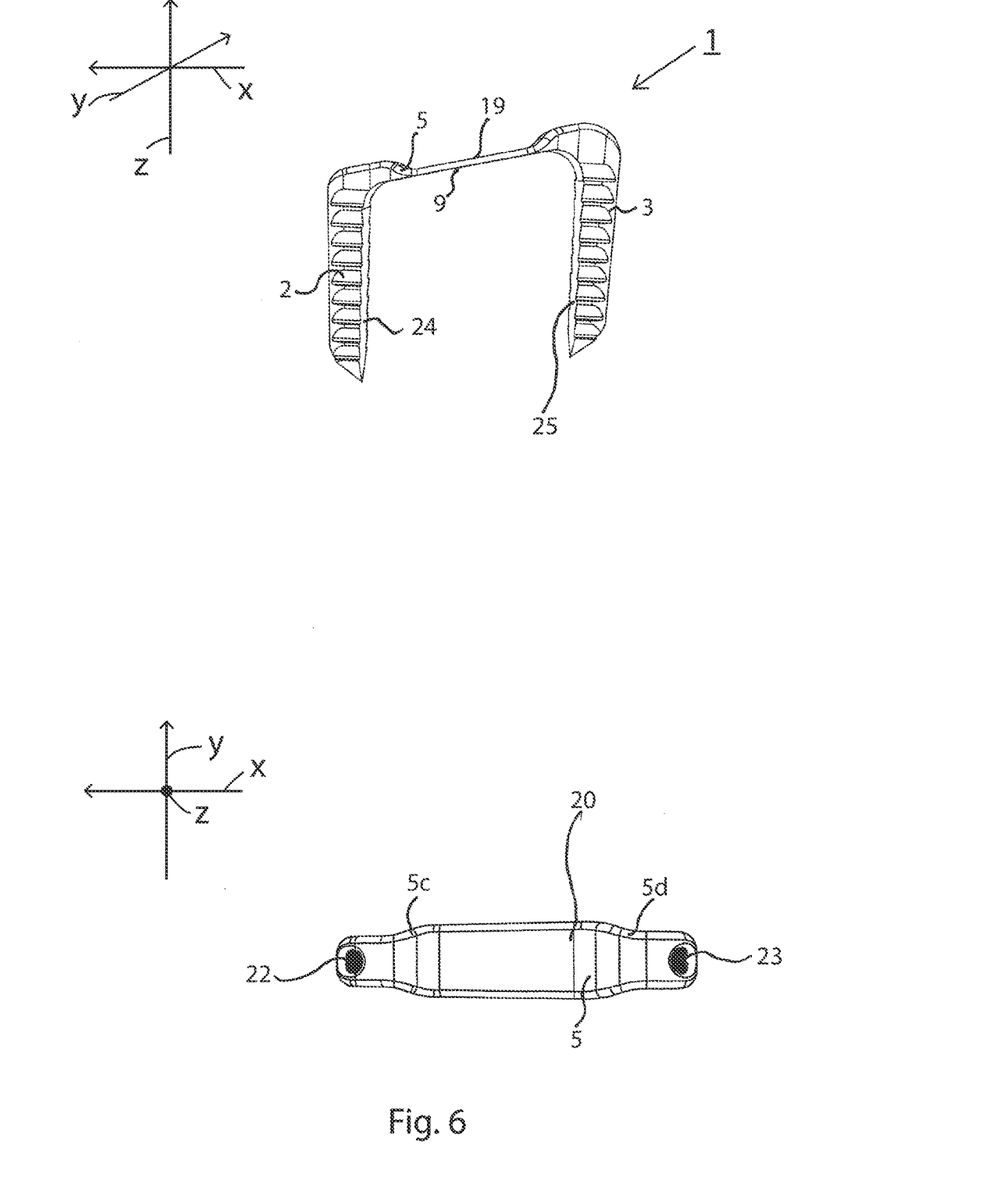
FIG. 6 shows schematic views of the further staple implant of FIG. 5, from the front and from above.
Figure 7:
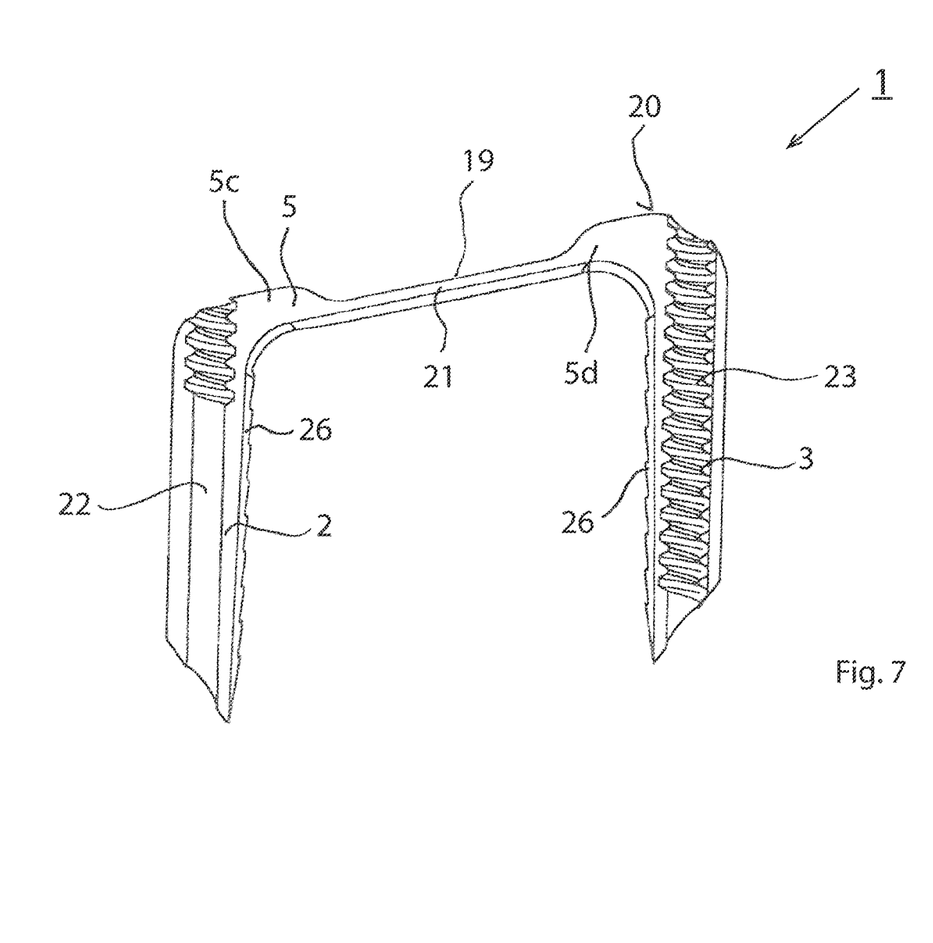
FIG. 7 shows a schematic cross-sectional view of the further staple implant of FIG. 5.
Figure 8:
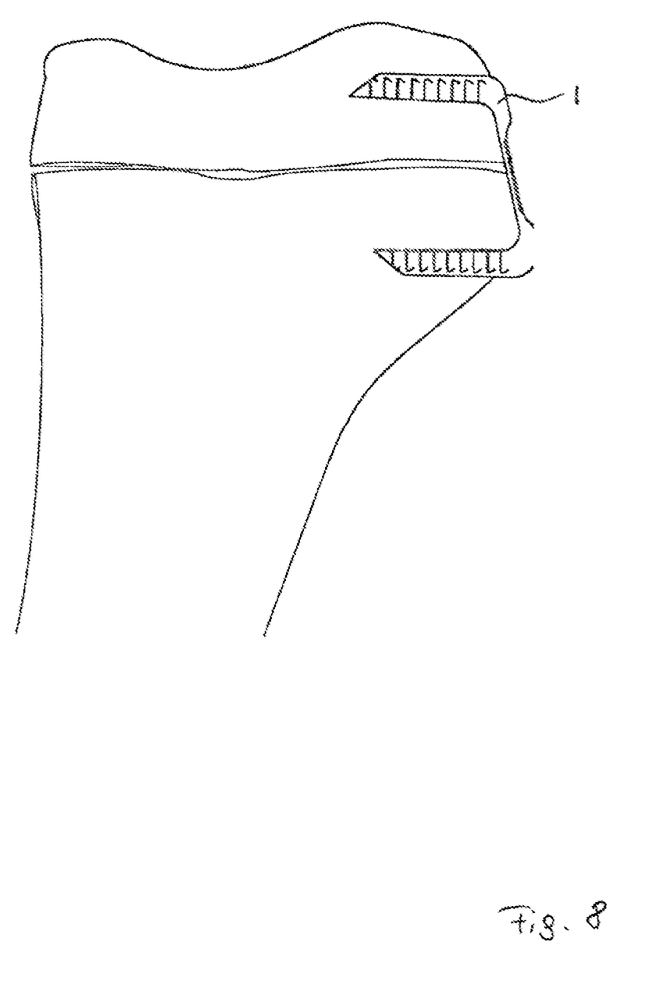
FIG. 8 shows a schematic view of an arrangement with a bone region bordering an epiphyseal plate and with an implanted staple implant.
Figure 9:
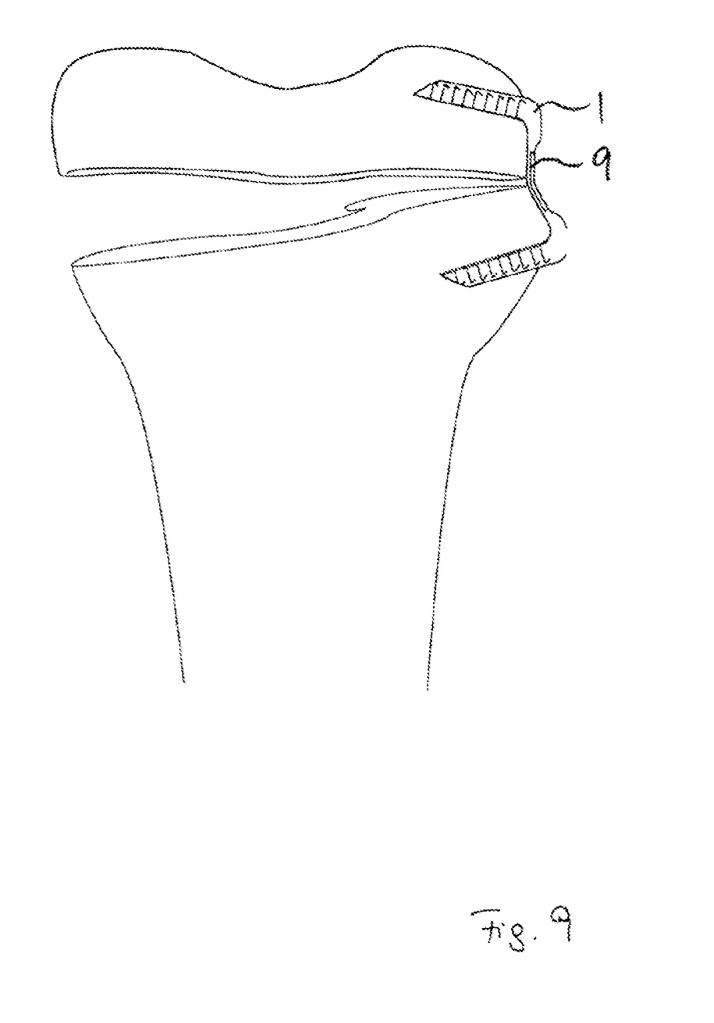
FIG. 9 shows a schematic view of the arrangement from FIG. 8, with the staple implant now bent in the area of the transverse web.

In the further embodiment of the staple implant 1 in FIGS. 4 to 9, the two anchoring limbs 2, 3 are offset parallel to each other in such a way that a trapezoid shape is obtained, as can also be seen in particular from FIG. 7.

Viewed from above, the transverse web 5 of the further staple implant 1 is designed in the central area 21 with a greater web width than at the ends 5c, 5d, with the widening of the central area decreasing continuously toward the ends 5c 5d.

As will be seen from FIG. 5 in particular, the anchoring limbs 2, 3 have flat inner sides 24, 25 which, in contrast to other surface areas of the two anchoring limbs 2, 3, do not have anchoring means 26. The anchoring means 26, which are designed over the length of the anchoring limbs 2, 3 in the embodiment shown, serve to anchor the staple implant 1 after the implantation. To deliberately remove the staple implant 1, a tool can be screwed into the internal thread of the through-channels.

The features disclosed in the above description, in the claims and in the drawing may be of importance, both individually and also in any desired combination, for the implementation of the various embodiments.

The invention claimed is:

1. A staple implant contoured relative to longitudinally extending x, laterally extending y, and vertically depending z axes lying perpendicular to each other and configured for insertion into a bone at a staple area for influencing growth in bone regions bordering an epiphyseal plate, the staple implant comprising:
   a transverse web having a longitudinal axis extending along the x axis and including a top surface, a bottom surface, a pair of side portions, and opposed ends, and
   a pair of anchoring limbs having limb axes extending parallel to each other along the z axis and transverse to the longitudinal axis of the transverse web, the anchoring limbs, at least when viewed in an xz plane defined by the x and z axes, including upper ends connected to the opposed ends of the transverse web and parallel inner and outer surfaces which extend from the opposed ends and taper downwardly symmetrically about the limb axes in a direction away from the transverse web to form fixation points at lower ends of the anchoring limbs which are configured to be inserted by impaction in the bone regions on opposite sides of the epiphyseal plate,
   wherein a pair of blind bores formed with internal threading is provided in the upper ends of the anchoring limbs in alignment with the limb axes above the longitudinal axis and open into the top surface of the transverse web at the opposed ends thereof, the blind bores with internal threading being adapted to secure one of an extraction instrument or an impaction instrument,
   wherein the transverse web is formed with a tapered zone located centrally between the side portions and provided by at least one concave formation extending inwardly from at least one of the top surface and the bottom surface of the transverse web in the direction of the x and z axes, the tapered zone extending symmetrically about the longitudinal axis of the transverse web and defining a bending area configured to be plastically deformable upon insertion of the staple implant in the bone to provide expansion of the anchoring limbs away from each other as a result of growth forces acting upon the epiphyseal plate opposite the staple area, wherein engagement structure in the form of spaced apart beads or recesses is formed on front and rear faces of the side portions of the transverse web in linear alignment with one another on opposite lateral sides of the at least one concave formation, and adapted to engage with the impaction instrument,
   wherein the transverse web has a thickness measured in a direction along the z axis which varies along a length of the at least one concave formation located between the spaced apart beads or recesses, and
   wherein at least the top surface of the transverse web extending over the side portions and the at least one concave formation has a width measured along the y axis which is constant.

2. The staple implant as claimed in claim 1, made of a superplastic material having grain sizes of between 1 nm and 1 μm.

3. The staple implant as claimed in claim 1, wherein the bending area of the at least one tapered zone is provided with a cross section that can be easily separated with a separating instrument.

4. The staple implant as claimed in claim 1, wherein the transverse web and the anchoring limbs are provided with different cross-sectional shapes.

5. A staple implant contoured relative to longitudinally extending x, laterally extending y and vertically extending z axes lying perpendicular to each other and configured for insertion into a bone at a staple area for influencing growth in bone regions bordering an epiphyseal plate, the staple implant comprising:
- a transverse web having a longitudinal axis extending along the x axis, and including a top surface, a bottom surface, a pair of side portions and opposed ends, and
- a pair of anchoring limbs having limb axes extending away from the transverse web relative to the z axis, the anchoring limbs including upper ends connected to the opposed ends of the transverse web, and peripheral surfaces which extend downwardly in a direction away from the transverse web to form fixation points at lower ends of the anchoring limbs which are arranged to be inserted in the bone regions on opposite sides of the epiphyseal plate, outer areas of the peripheral surfaces being formed with anchoring structure along entire outer lengths of the anchoring limbs and the peripheral surfaces being formed with flat, inner sides along entire lengths of the anchoring limbs, the respective flat, inner sides facing inwardly towards each other with respect to the longitudinal axis,
- wherein a pair of through channels formed with internal threading extends through the anchoring limbs in alignment with the limb axes and open into the top surface of the transverse web at the opposed ends thereof, the through channels with internal threading being adapted to secure an extraction instrument,
- wherein the transverse web is formed with a tapered zone located centrally between the side portions and provided by a depression having a flat profile with a constant thickness measured in a direction along the z axis, the tapered zone defining a bending area configured to be plastically deformable upon insertion of the staple implant in the bone to provide expansion of the anchoring limbs away from each other as a result of growth forces acting upon the epiphyseal plate opposite the staple area, and
- wherein, when viewed from above in an xy plane defined by the x and y axes, the transverse web in a central area has a width measured in the direction of the y axis which is wider than a width of the transverse web at the opposed ends at the top surface.

\* \* \* \* \*